United States Patent [19]

Pla et al.

[11] 4,302,445

[45] Nov. 24, 1981

[54] METHOD FOR CONCENTRATING AND PURIFYING ANTIHEMOPHILIC FACTOR OR FACTOR VIII

[75] Inventors: Jean F. Pla, Ste Foy les Lyons; Jacques C. Liautaud, Limonest, both of France

[73] Assignee: Institut Merieux, Lyons, France

[21] Appl. No.: 113,283

[22] Filed: Jan. 18, 1980

[51] Int. Cl.$^3$ ............................................. A61K 35/14
[52] U.S. Cl. ................................................. 424/101
[58] Field of Search ................... 424/101; 260/112 R

[56] References Cited

U.S. PATENT DOCUMENTS

| | | | |
|---|---|---|---|
| 4,104,266 | 8/1978 | Wickerhauser | 424/101 |
| 4,170,639 | 10/1979 | Liu et al. | 424/101 |
| 4,188,318 | 2/1980 | Shanbrom | 424/101 |

OTHER PUBLICATIONS

Wickerhauser et al. –Vox Sanguinis, vol. 35 (1978) pp. 18–31.

Primary Examiner—Sam Rosen
Attorney, Agent, or Firm—Cushman, Darby & Cushman

[57] ABSTRACT

A method is disclosed for concentrating and purifying antihemophilic factor (AHF or Factor VIII), a cryoprecipitate is collected from frozen human plasma and cold washed with pyrogen-free distilled water or water saline. The washed cryoprecipitate is extracted with pyrogen-free distilled water, the prothrombin complex is removed and the fibrinogen is precipitated. The remaining purified solution is ultrafiltered to form a highly concentrated Factor VIII solution.

9 Claims, No Drawings

METHOD FOR CONCENTRATING AND PURIFYING ANTIHEMOPHILIC FACTOR OR FACTOR VIII

BACKGROUND OF THE INVENTION

Several methods have been described for the production of antihemophilic factor (AHF or Factor VIII) for therapeutic use. Such methods generally start from blood plasma cryoprecipitates and involve the extraction of Factor VIII by suitable extraction agents, possibly followed by purification steps.

One of said methods is described in British patent specification No. 1,551,928 and comprises the steps of extracting cryoprecipitate in pyrogen-free water at room temperature, removing denatured proteins and prothrombin complex from the extracted solution by adsorption, precipitating fibrinogen from the low ionic strength liquid extract by cooling the liquid to about 1° C. to 2° C., and lyophilizing the supernatant liquid to obtain the Factor VIII concentrate.

The above-mentioned method results in a liquid concentrate with a Factor VIII concentration generally comprised between 10 and 14 I.U. (International Units) per ml. However there is a need for higher concentrations for several reasons. For example, it would be very desirable to obtain 100 ml vials containing 1000 units of lyophilized Factor VIII but the volume of liquid Factor VIII concentrate to be dried would be too large to allow use of such vials.

Concentrating such product should be possible by dissolving a lyophilized powder in a small volume and then re-drying, or by the use of ultra-filtration. But the high proteic content of the resulting solutions would give a final lyophilized powder with poor solubility.

Another of such methods is described in the Wickerhauser U.S. Pat. No. 4,104,266 and provides a first extraction of a cryoprecipitate with a low ionic strength buffer solution comprising tris(hydroxymethyl)aminomethane at a temperature of about 0° C. to obtain a cold insoluble fraction having cold soluble impurities removed therefrom, followed by the step of extracting said cold insoluble fraction with a similar buffer solution at a temperature of about 21° C. to obtain a solution comprising the Factor VIII. In fact the Factor VIII concentration before lyophilizing seems limited to about 8 to 10 I.U. per ml.

It is an object of the present invention to provide a new and useful improvement for preparation of a Factor VIII concentrate from a cryoprecipitate whereby a higher Factor VIII concentration is obtained of at least 20 to 25 I.U. per ml.

Another object of the present invention is to obtain lyophilized Factor VIII vials containing at least 1000 to 1400 I.U. per 100 ml. vial.

Another object of the present invention is to obtain such lyophilized Factor VIII allowing a short dissolution time, even when reducing the amount of fluid used for reconstitution in order to shorten infusion time.

Another object of the present invention is to increase the removal of proteic impurities, including fibrinogen, without significantly decreasing the final yield of Factor VIII.

Another object of the present invention is to provide such an improvement able to be performed on an industrial scale for treating cryoprecipitate collected from more than 100 l and even more than 1000 l of plasma.

Another object of the present invention is to improve a method of preparation of a Factor VIII concentrate according to British patent specification No. 1,551,928.

DETAILED DESCRIPTION OF THE INVENTION

The method of the present invention comprises the steps of cold washing the cryoprecipitate with one of the agents selected from the group consisting of pyrogen-free distilled water and water saline and therefter ultra-filtering the purified Factor VIII concentrate in order to increase its concentration.

The step of cold washing the cryoprecipitate is advantageously conducted at a temperature between −1° C. and +5° C. and preferably between +0.5° and +1.5° C.

The volume of washing agent can be determined by simple assays. It may be advantageously comprise from 2 to 6 times the weight of cryoprecipitate (ml/g) and preferably 4 times.

The water saline consists of a water solution comprising pyrogen free distilled water at a concentration of sodium chloride varying from more than 0 to 15 g/l and preferably of 9 g/l.

The ultra-filtration step is achieved by using usual ultra-filtration means adapted to proteic concentration as for example Millipore filters, type PTHK (Nominal Molecular Weight Limit=100,000 Dalton).

Owing to the method of the invention a Factor VIII product with 25 I.U./ml of AHF can readily be obtained, allowing lyophilization in 100 ml vials containing at least 1000 I.U. or 50 ml vials containing at least 500 I.U. If desirable a much more concentrated product can be obtained, for example at least 1,000 I.U. in a 50 ml vial. Redissolution time of the lyophilized product is generally less than 5 minutes when dissolved in water for injection.

EXAMPLE 1

A cryoprecipitate of 183 l of frozen human plasma is collected according to British patent specification No. 1,551,928. The weight of the cryoprecipitate is 1.3 kg.

5.2 l of pyrogen free water saline 9% are chilled to a temperature from 0° to +1.5° C. The cryoprecipitate is ground and suspended in the water saline. The suspension is submitted to agitation at from 0.5° to 1.5° C. for 15 minutes. The washed cryoprecipitate is recovered by centrifugation or decantation and squeezing, and the yellow supernatant is discarded.

The supernatant liquid contains pigmentar and proteic material with a protein content of 2.15 g/l. A portion of 0.17 I.U. of AHF per ml is lost with the supernatant, which corresponds to a loss of 4.6 I.U./l of original plasma.

The washed cryoprecipitate (1.48 kg) is then submitted to a known extraction and purification method described in the above mentioned British patent specification which can be summarized as follows:

The cryoprecipitate is suspended in pyrogen free water at room temperature to form a 3.8 l suspension and the pH is adjusted to about 7. The AHF concentration in the suspension is of 20.4 I.U./ml, that is 76,908 I.U. Thereafter aluminium hydroxide is added and the pH re-adjusted to about 6.9 to 7. The aluminium hydroxide is allowed to adsorb for 10 to 15 minutes under stirring to adsorb prothrombin complex. The mixture is then chilled to a temperature from about +1° to about +7° C. for ¼ to 2 hours and the heavy precipitate which forms is removed by centrifugation, thus eliminating excessive amounts of fibrinogen.

The remaining solution is then clarified by passing successively the liquid through 293 mm non-fibrous membrane filters having 1.20, 0.65, 0.45 and 0.30 nm diameter pores or an equivalent system using filtration cartridges.

The remaining solution (2.92 l) with a content of 16 I.U./ml i.e. 46,720 I.U. is then submitted to the ultrafiltration step as follows: the clarified solution is concentrated by passing through an ultra-filtration Millipore cassette PTHK D0005 system. The cassette system is rinsed with a citrate glycine buffer with pH of about 6.8. The concentrate solution is then sterilized by filtering the liquid through an autoclaved non-fibrous 293 mm membrane having 0.3 nm diameter pores. The initial solution volume is thus reduced to 1.90 , with a Factor VIII content of 25 I.U./ml. The ultrafiltrate contains substantially no Factor VIII (AHF). The total yield amounts to 47,500 I.U.

The protein content is 16.41 g/l and the fibrinogen 8.14 g/l, that is respectively 656 mg/1,000 I.U. and 326 mg per 1,000 I.U.

Thereafter the concentrated AHF solution is filled preferably in 100 ml vials and lyophilized.

After lyophilization the Factor VIII content per vial amounts to 1,033 I.U.

The dissolution time of the lyophilized product is about 5 minutes in 50 ml of water for injection.

A standard method, according to Example 1 but omitting the steps of cold washing the cryoprecipitate and ultra-filtering the solution, usually leads to a 100 ml vial content of only 500 I.U. If the utla-filtration step is present and the sole cold washing step is omitted, a higher content is obtained but the redissolution time is increased to undesirable values.

EXAMPLE 2

A human plasma cryoprecipitate weighing 11.1 kg and collected from 1,485 l of plasma is treated according to the method of Example 1. The washing step is conducted with 44.5 l water saline (NaCl=9 g/l). The discarded solution contains 0.4 I.U. per ml which corresponds to 10.7 I.U. per liter of starting plasma, and 6 g/l of unwanted proteins. The washed cryoprecipitate which weighs 13.1 kg is suspended in water to form a 28.8 l suspension containing 475,200 I.U. and added with aluminium hydroxide. The 27.85 l clarified solution (AHF=14.5 I.U./ml i.e. 403,825 I.U.) is reduced by ultra-filtration to 16.0 l (AHF=24.7 I.U./ml i.e. 395,200 I.U.). The total protein content is 14.1 g/l which corresponds to 571 mg per 1,000 I.U. The fibrinogen amount is 6.6 g/l i.e. 267 mg per 1,000 I.U.

EXAMPLE 3

A 3.75 kg cryoprecipitate is collected from 439 l of plasma. 15 l of pyrogen free water are chilled to a temperature from 0° to +1.5° C. The cryoprecipitate is ground and suspended in the pyrogen free water. The suspension is submitted to stirring at from 0.5° to 1.5° C. for 15 minutes.

The washed cryoprecipitate is recovered as in Example 1 and weighs 4.75 kg. The discarded 14 l supernatant contains 1.8 I.U. per ml and 7.5 g/l of unwanted proteins.

The washed cryoprecipitate is then submitted to the remaining steps of Example 1:

suspended cryoprecipitate: 11.9 l with 11.4 I.U./ml AHF (135,660 total I.U.);
adsorbed clarified solution: 11.2 l with 9.2 I.U./ml (103,040 I.U.);
adsorbed ultra-filtered solution: 4.0 l with 23.5 I.U./ml AHF (i.e. 94,000 I.U.);
lyophilized 100 ml vial: 1013 I.U. AHF; dissolution time in 50 ml is 5 minutes.

The amount of proteins is generally reduced from 1300 to 1400 mg/1000 I.U. in the conventional methods to about 600 to 700 mg/1000 I.U. according to the invention.

The amount of fibrinogen is generally reduced from about 600 mg/1000 I.U. in the conventional methods to about 400 mg/1000 I.U. in the method according to the invention.

After lyophilization the amount of AHF is of about 1000 to 1400 I.U. per 100 ml vial, corresponding to a yield of 200–240 I.U. per liter of original plasma. Assays of redissolution in vials show as described a redissolution time of about 5 minutes or less when th e powder is reconstituted to its original volume. The product can also be redissolved in half its volume in less than 10 minutes, thus reaching a Factor VIII concentration of 40 to 50 I.U./ml.

All concentrates prepared by this procedure have been found $HB_s$ Ag negative and generally meet all other FDA requirements for biological products including sterility, identity and pyrogenicity.

Hemagglutinin levels are not higher in the highly concentrated new product than in the routine product of low AHF concentration, suggesting that a portion of the hemaggultinins is discarded during the washing step.

The lyophilized products obtained by the method according to the invention are suitable for administration to hemophilic patients and have shown excellent in vivo recovery and biological half-life.

Notwithstanding the high Factor VIII level the AHF preparation according to the invention is, when dissolved, generally less colored than the known less concentrated AHF solutions, due to a better elminiation of pigments. No toxicity or undesirable side effects have so far been reported.

What we claim is:

1. In a method of concentrating and purifying Factor VIII comprising the steps of (1) collecting cryoprecipitate from frozen human plasma, (2) extracting the cryoprecipitate, (3) removing prothrombin complex, (4) precipitating fibrinogen and thereafter (5) ultra-filtering the remaining solution to form a purified Factor VIII concentrate,
   the improvement consisting of cold washing the cryoprecipitate before extraction step (2) with an aqueous saline solution.

2. In a method of concentrating and purifying Factor VIII consisting essentially of the steps of (1) collecting cryoprecipitate from frozen human plasma, (2) extracting the cryoprecipitate in pyrogen-free water at room temperature at a pH of about 7, (3) adding aluminum hydroxide to adsorb prothrombine complex and adjusting the pH to about 7, (4) cooling the mixture to a temperature of from about +1° to about +7° C. and thereafter (5) removing the thus-formed fibrinogen-containing precipitate to obtain a Factor VIII concentrate,
   the improvement comprising steps of cold washing the cryoprecipitate before extraction steps (2) with an aqueous saline solution, and by ultra-filtering the Factor VIII concentrate obtained in step (3).

3. A method as claimed in claim 1 or 2 wherein said cold washing step is conducted at a temperature of between −1° C. and +1.5° C.

4. A method as claimed in claim 3 wherein said cold washing step is conducted at a temperature between −0.5° C. and +1.5° C.

5. A method as claimed in claim 1 or 2 wherein said saline solution contains at most 15 g/l of sodium chloride dissolved therein.

6. A method as claimed in claim 5 wherein said saline solution contains about 9 g/l of sodium chloride dissolved therein.

7. A method as claimed in claim 1 or 2 wherein said cryoprecipitate is ground and added to the saline solution to form a suspension which is agitated for about 15 minutes.

8. A method as claimed in claim 1 or 2 including the additional step of lyophilizing the ultra-filtered purified Factor VIII concentrate.

9. A method as claimed in claim 8 wherein said concentrate is lyophilized in 100 ml vials each containing at least 1000 I.U. Factor VIII per vial.

* * * * *

UNITED STATES PATENT AND TRADEMARK OFFICE
CERTIFICATE OF CORRECTION

PATENT NO. : 4,302,445

DATED : November 24, 1981

INVENTOR(S) : PLA, et al

It is certified that error appears in the above-identified patent and that said Letters Patent are hereby corrected as shown below:

Claim 2, line 14, delete "(3)" insert --(5)--.

Signed and Sealed this

Twentieth Day of April 1982

[SEAL]

Attest:

*Attesting Officer*

GERALD J. MOSSINGHOFF

*Commissioner of Patents and Trademarks*